(12) United States Patent
Druma

(10) Patent No.: US 11,744,630 B2
(45) Date of Patent: Sep. 5, 2023

(54) TUMOR ABLATION SYSTEM

(71) Applicant: MEDTRONIC HOLDING COMPANY SÀRL, Tolochenaz (CH)

(72) Inventor: Calin Druma, San Jose, CA (US)

(73) Assignee: MEDTRONIC HOLDING COMPANY SÀRL, Tolochenaz (CH)

( * ) Notice: Subject to any disclaimer, the term of this patent is extended or adjusted under 35 U.S.C. 154(b) by 1152 days.

(21) Appl. No.: 16/269,997

(22) Filed: Feb. 7, 2019

(65) Prior Publication Data
US 2019/0167333 A1 Jun. 6, 2019

Related U.S. Application Data

(62) Division of application No. 14/593,542, filed on Jan. 9, 2015, now Pat. No. 10,231,770.

(51) Int. Cl.
*A61B 18/18* (2006.01)
*A61B 18/04* (2006.01)
(Continued)

(52) U.S. Cl.
CPC .......... *A61B 18/04* (2013.01); *A61B 17/8805* (2013.01); *A61B 17/8825* (2013.01);
(Continued)

(58) Field of Classification Search
CPC ..... A61B 18/04; A61B 18/1482; A61B 18/14; A61B 18/1487; A61B 18/18; A61B 18/1815; A61B 2018/1823; A61B 2018/046; A61B 2018/183; A61B 2018/1869; A61B 2018/1892; A61B 2018/00005; A61B 2018/00011; A61B 2018/00023; A61B 2018/00214;
(Continued)

(56) References Cited

U.S. PATENT DOCUMENTS 3,211,150 A 10/1965 Foderick
4,773,393 A 9/1988 Haber et al.
(Continued)

FOREIGN PATENT DOCUMENTS

DE 10010467 9/2001
EP 1313411 10/2007
(Continued)

OTHER PUBLICATIONS

International Search Report dated Aug. 8, 2017 of corresponding International Application No. PCT/US2017/029330.
(Continued)

*Primary Examiner* — Thomas A Giuliani

(57) ABSTRACT

A system for use in tumor ablation. The tumor ablation system includes a microwave antenna which has a channel along the length thereof. There are two ports proximate the proximal end of the microwave antenna. The first port is an energy port configured to connect the antenna to an energy source. The second port is a fluid port configured to connect the channel to a fluid delivery mechanism. The system also includes an inflatable balloon configured to be attached to a distal end of the antenna. The channel permits fluid access from the fluid port to an interior of the balloon for inflation thereof.

20 Claims, 3 Drawing Sheets

(51) Int. Cl.
*A61B 17/88* (2006.01)
*A61B 18/00* (2006.01)
*A61B 17/00* (2006.01)

(52) U.S. Cl.
CPC .......... *A61B 17/8855* (2013.01); *A61B 18/18* (2013.01); *A61B 18/1815* (2013.01); *A61B 2017/00057* (2013.01); *A61B 2017/00084* (2013.01); *A61B 2018/0022* (2013.01); *A61B 2018/00023* (2013.01); *A61B 2018/0025* (2013.01); *A61B 2018/00166* (2013.01); *A61B 2018/00232* (2013.01); *A61B 2018/00339* (2013.01); *A61B 2018/00565* (2013.01); *A61B 2018/00577* (2013.01); *A61B 2018/00791* (2013.01); *A61B 2018/00809* (2013.01); *A61B 2018/00821* (2013.01); *A61B 2018/046* (2013.01); *A61B 2018/183* (2013.01); *A61B 2018/1823* (2013.01); *A61B 2018/1861* (2013.01); *A61B 2018/1869* (2013.01); *A61B 2018/1892* (2013.01)

(58) Field of Classification Search
CPC .. A61B 2018/0022; A61B 2018/00273; A61B 2018/00279; A61B 2018/00285; A61B 2018/00339; A61B 2018/00565; A61B 2018/00577; A61B 2018/00994; A61B 2018/044; A61B 2018/1838; A61B 2018/1861; A61B 2018/00332; A61B 2018/0025; A61B 17/8805; A61B 17/8855
USPC ........ 606/33, 41; 607/98, 99, 101, 104, 105, 607/115, 116, 154, 156
See application file for complete search history.

(56) References Cited

U.S. PATENT DOCUMENTS

| | | | |
|---|---|---|---|
| 4,921,483 A | 5/1990 | Wijay et al. | |
| 5,057,106 A | 10/1991 | Kasevich et al. | |
| 5,540,679 A | 6/1996 | Fram et al. | |
| 5,843,116 A | 12/1998 | Crocker et al. | |
| 6,129,737 A | 10/2000 | Hamilton et al. | |
| 6,230,060 B1 | 5/2001 | Mawhinney | |
| 6,241,727 B1 | 6/2001 | Tu | |
| 6,352,551 B1 | 3/2002 | Wang | |
| 6,364,900 B1 | 4/2002 | Heuser | |
| 6,416,457 B1 | 7/2002 | Urick et al. | |
| 6,427,089 B1* | 7/2002 | Knowlton | A61B 18/18 607/101 |
| 6,458,096 B1 | 10/2002 | Briscoe | |
| 6,488,653 B1 | 12/2002 | Lombardo | |
| 6,527,739 B1 | 3/2003 | Bigus et al. | |
| 6,544,224 B1 | 4/2003 | Steese-Bradley | |
| 6,847,848 B2 | 1/2005 | Sterzer et al. | |
| 6,911,038 B2 | 6/2005 | Mertens | |
| 6,951,569 B2 | 10/2005 | Nohilly et al. | |
| 7,197,363 B2 | 3/2007 | Prakash et al. | |
| 7,261,720 B2 | 8/2007 | Stevens et al. | |
| 7,537,580 B2 | 5/2009 | Willard | |
| 7,826,904 B2 | 11/2010 | Appling et al. | |
| 8,221,349 B2 | 7/2012 | Auyoung et al. | |
| 8,241,335 B2 | 8/2012 | Truckai et al. | |
| 8,382,746 B2 | 2/2013 | Williams | |
| 8,679,106 B2* | 3/2014 | Ormsby | A61B 18/1492 606/41 |
| 8,708,955 B2* | 4/2014 | Tilson | A61M 25/0147 604/103.1 |
| 8,945,107 B2 | 2/2015 | Buckley et al. | |
| 2002/0120229 A1 | 8/2002 | Miles et al. | |
| 2003/0130664 A1 | 7/2003 | Boucher et al. | |
| 2003/0195499 A1* | 10/2003 | Prakash | A61B 17/29 606/33 |
| 2004/0092948 A1 | 5/2004 | Stevens et al. | |
| 2004/0106999 A1 | 6/2004 | Mathews | |
| 2004/0133254 A1* | 7/2004 | Sterzer | A61B 18/18 607/101 |
| 2004/0186471 A1 | 9/2004 | Trieu | |
| 2005/0165389 A1* | 7/2005 | Swain | A61B 18/1815 606/27 |
| 2005/0245896 A1 | 11/2005 | Kucharczyk et al. | |
| 2006/0034886 A1 | 2/2006 | Ward et al. | |
| 2007/0149963 A1 | 6/2007 | Matsukuma et al. | |
| 2008/0249604 A1 | 10/2008 | Donovan | |
| 2009/0088788 A1 | 4/2009 | Mouw | |
| 2009/0254064 A1 | 10/2009 | Boatman | |
| 2009/0299327 A1 | 12/2009 | Tilson | |
| 2009/0299373 A1 | 12/2009 | Sisken | |
| 2009/0299401 A1* | 12/2009 | Tilson | A61B 17/8816 606/192 |
| 2010/0004650 A1 | 1/2010 | Ormsby | |
| 2010/0321192 A1 | 12/2010 | Brannan | |
| 2011/0028981 A1 | 2/2011 | McKay | |
| 2011/0106184 A1 | 5/2011 | Sapida et al. | |
| 2011/0125148 A1 | 5/2011 | Turner | |
| 2011/0202064 A1 | 8/2011 | O'Halloran et al. | |
| 2011/0319880 A1 | 12/2011 | Prakash | |
| 2012/0165941 A1 | 6/2012 | Rabiner | |
| 2012/0197319 A1 | 8/2012 | Auyoung et al. | |
| 2012/0197321 A1 | 8/2012 | Donovan | |
| 2012/0203220 A1 | 8/2012 | Brannan et al. | |
| 2012/0259326 A1 | 10/2012 | Brannan | |
| 2012/0296273 A1 | 11/2012 | Arana et al. | |
| 2013/0053880 A1 | 2/2013 | Bouasaysy et al. | |
| 2013/0144298 A1 | 6/2013 | Choi | |
| 2013/0237950 A1 | 9/2013 | Gianotti | |
| 2013/0238038 A1 | 9/2013 | Auyoung | |
| 2013/0256302 A1 | 10/2013 | Chu | |
| 2013/0261729 A1 | 10/2013 | Gillick et al. | |
| 2013/0304182 A1 | 11/2013 | Pacetti et al. | |
| 2014/0128877 A1 | 5/2014 | O'Halloran | |
| 2014/0276572 A1 | 9/2014 | Auyoung et al. | |
| 2014/0277466 A1 | 9/2014 | Teisen et al. | |
| 2014/0303633 A1 | 10/2014 | O'Halloran et al. | |
| 2014/0303730 A1 | 10/2014 | McGuire et al. | |
| 2014/0316411 A1 | 10/2014 | Day | |
| 2014/0371652 A1 | 12/2014 | Aramaki et al. | |
| 2014/0371672 A1 | 12/2014 | Pinchuk et al. | |
| 2015/0342660 A1 | 12/2015 | Nash | |
| 2015/0359432 A1 | 12/2015 | Ehrenreich | |
| 2017/0367747 A1 | 12/2017 | Druma | |
| 2019/0110826 A1 | 4/2019 | Goshayeshgar et al. | |
| 2019/0118004 A1* | 4/2019 | Diederich | A61N 7/02 |

FOREIGN PATENT DOCUMENTS

| | | |
|---|---|---|
| EP | 2853210 | 4/2015 |
| WO | 217801 A2 | 3/2002 |
| WO | 217801 A3 | 3/2002 |
| WO | 2006053312 | 5/2006 |
| WO | 2008026888 | 3/2008 |
| WO | 2013074933 | 5/2013 |

OTHER PUBLICATIONS

European Search Search and Opinion for EP17177266 the counterpart application dated Nov. 16, 2017, 9 pages.
Supplementary European Search Report dated Nov. 18, 2019 of corresponding European Application No. 17790239.2.
Examination Report dated Jan. 28, 2021 of European Application No. 17790239.2.
International Search Report and Written Opinion dated May 6, 2021 of International Application No. PCT/US2021/019442.
Supplementary European Search Report dated Jul. 11, 2018 of corresponding European Application No. 16735443.0.

(56) References Cited

OTHER PUBLICATIONS

Examination Report dated Aug. 5, 2019 of corresponding Australian Application No. 2016205167.

* cited by examiner

TUMOR ABLATION SYSTEM

CROSS-REFERENCE TO RELATED APPLICATIONS

This application is a divisional of U.S. application Ser. No. 14/593,542, now U.S. Pat. No. 10,231,770, filed Jan. 9, 2015, all of which is incorporated by reference herein.

BACKGROUND OF THE INVENTION

The present invention relates generally to a tumor ablation system.

Description of the Related Art

Spinal metastases are the most common cause of severe pain among patients with cancer. Spinal metastases are also often accompanied by vertebral compression fractures.

Balloon kyphoplasty is a minimally invasive procedure designed to repair vertebral compression fractures by reducing and stabilizing the fractures. Reduction is accomplished by inserting at least one compliant balloon into the central portion of the fractured vertebral body. The balloon(s) are carefully inflated such that the cancellous bone is pushed out toward the cortical walls until the vertebral body returns to the correct height. After reduction, the balloons are deflated and removed. Stabilization is accomplished by filling the resulting cavities with bone cement. The bone cement hardens, forming an internal cast, stabilizing the fracture.

Radiofrequency ablation is used for the destruction of unwanted tissue, including tumors. During radiofrequency ablation, a probe is inserted into the unwanted tissue. A plurality of small electrodes are deployed from the end of the probe to encompass the unwanted tissue. The opposite end of the probe is connected to a radiofrequency generator which sends radiofrequency energy through the electrodes causing the immediately adjacent tissue to heat up. Once the unwanted tissue reaches a sufficient temperature for a specific period of time, the tissue dies. Radiofrequency ablation of a tumor takes about 20-30 minutes.

Microwave ablation is also used for the destruction of unwanted tissue, including tumors. During microwave ablation, a probe is inserted into the unwanted tissue. The other end of the probe is connected to a microwave generator which sends microwave energy through the end of the probe and causes the nearby tissue to heat up. Once the unwanted tissue reaches a sufficient temperature for a specific period of time, the tissue dies. Microwave ablation of a tumor takes about 10-15 minutes. However, the direct heating caused by the emitted microwave energy creates a risk of heating, and therefore damaging, the sensitive neural pathways adjacent the vertebral body.

Therefore, there is a need for an apparatus and method for quickly repairing vertebral compression fractures while ablating a tumor without causing damage to nearby neural pathways or other vital organs.

SUMMARY OF THE INVENTION

A microwave antenna, in accordance with the present invention, includes an inner conductor and an outer conductor separated by a dielectric. The outer conductor is surrounded by a shield. The dielectric includes a channel that extends along the length of the antenna and connects a fluid port at a proximal end of the antenna to an inflatable balloon attached to a distal end of the antenna. The fluid port is attached via tubing to a high pressure syringe filled with a mixture of saline and contrast material or simply with sterile water.

The proximal end of the antenna also includes a microwave port that facilitates the attachment of a microwave generator to the inner and outer conductors of the microwave antenna to enable the transmission of microwave energy from the microwave generator to the fluid in the balloon attached to the proximal end of the antenna and the adjacent tissue.

The method includes placing the patient in the prone position and making an incision in the skin. The surgeon inserts a cannula through the incision into contact with the bone that has a tumor. The surgeon introduces a drill through the cannula and creates an opening in the bone and into the tumor. Next, the surgeon inserts the antenna through the cannula to position the balloon in the opening. With the balloon in the opening, the surgeon depresses the plunger on the high pressure syringe, which forces saline and contrast material into the balloon. The saline inflates the balloon and presses against the tumor. With the balloon pressing against the tumor, the surgeon turns on the microwave generator. The microwave energy heats the mixture in the balloon, which conducts the heat into the tumor. Once the heat destroys the tumor, the microwave generator is turned off.

After the tumor is destroyed, the balloon is further inflated until the fracture is reduced. After reduction is achieved, the balloon is deflated and the resulting cavity is filled with bone cement for stabilization.

BRIEF DESCRIPTION OF THE DRAWINGS

The accompanying drawings, which are incorporated in and constitute a part of the specification, illustrate preferred embodiments of the invention and, together with the description, serve to explain the objects, advantages, and principles of the invention. In the drawings.

DETAILED DESCRIPTION OF THE PREFERRED EMBODIMENTS

Other embodiments of the invention will be apparent to those skilled in the art from consideration of the specification and practice of the invention disclosed herein. It is intended that the embodiments described below be considered as exemplary only, with a true scope and spirit of the invention being indicated by the appended claims.

The detailed description of the invention below is described for, and shown in the figures for, use in a fractured vertebral body V. However, it should be understood that the invention could be used for tumor ablation as well as reduction in any bone.

As shown in FIGS. 1-3A, a system 10 for use in tumor ablation includes a microwave antenna 20 and a balloon 50 configured to be attached to the distal end of antenna 20. Balloon 50 and the majority of the length of microwave antenna 20 is sized and configured to be inserted through a cannula 60 into an opening prepared in fractured vertebral body V.

Figure 2:
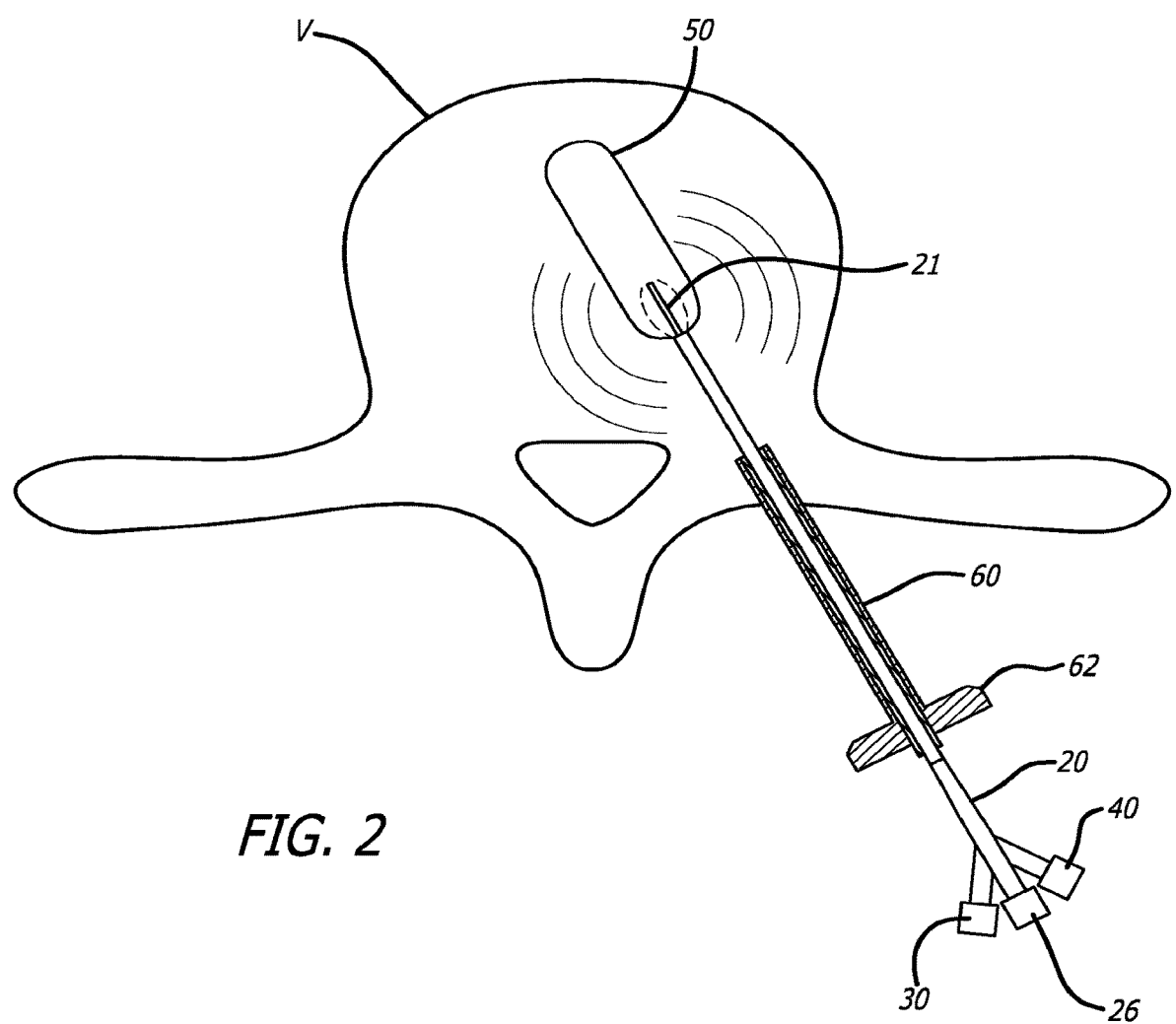
FIG. 2 is a partially cross-sectional plan view of the microwave antenna of the system shown in FIG. 1 for use in tumor ablation and vertebral compression fracture repair showing the balloon partially inflated inside the fractured vertebral body.
Figure 3A:
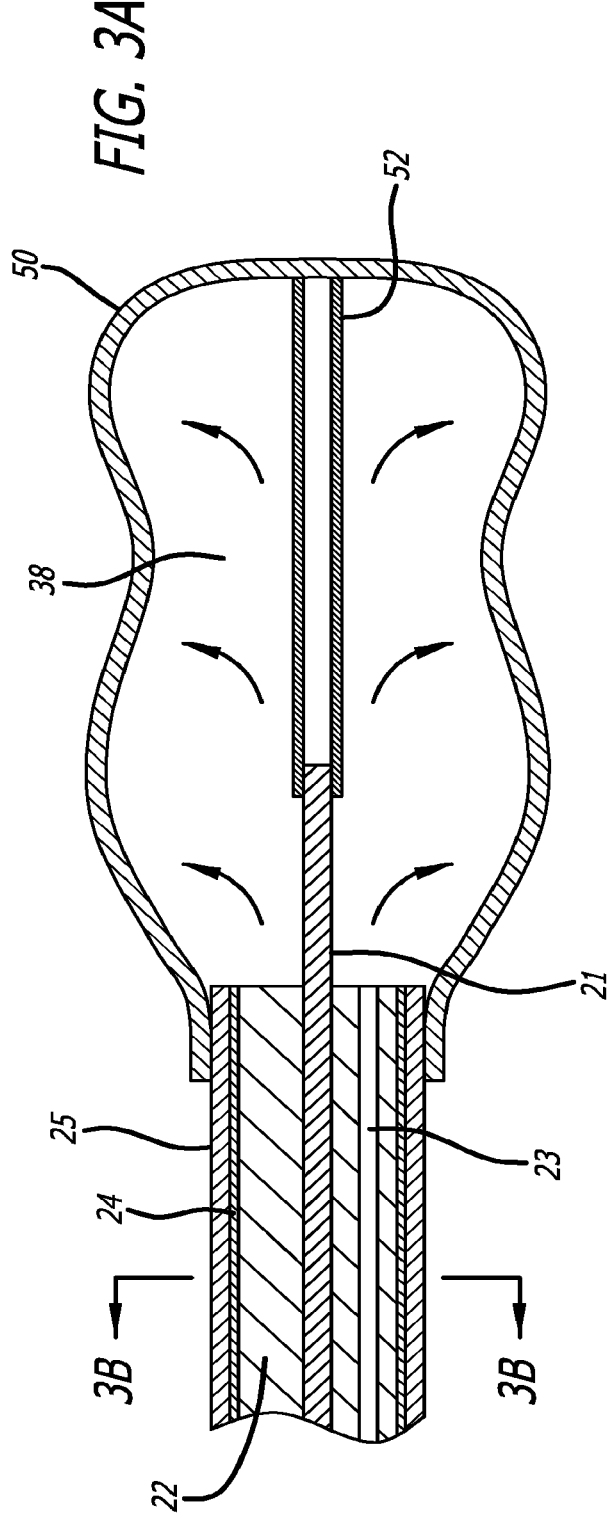
FIG. 3A is a cross-sectional view of the distal end of the microwave antenna for use in tumor ablation and vertebral compression fracture repair showing saline inflating the balloon.
Figure 3C:
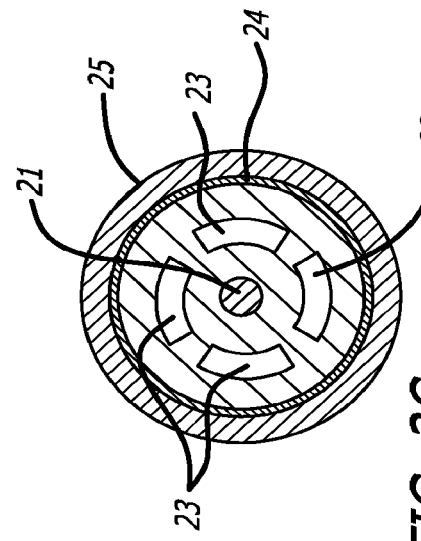
FIG. 3C is a cross-sectional view of an alternative embodiment of the antenna show in FIGS. 3A and 3B.
Figure 3B:
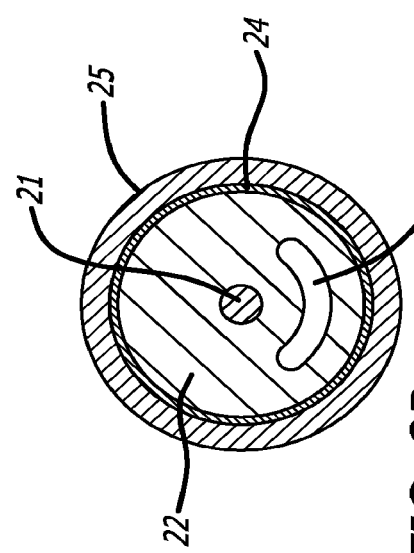
FIG. 3B is an enlarged cross-sectional view of the antenna show in FIG. 3A.

As shown in FIGS. 3A and 3B, antenna 20 includes an inner conductor 21 which extends along a length of antenna 20. Inner conductor 21 may be constructed of copper or any other conductive material suitable for transmission of microwave energy. Antenna 20 further includes a dielectric layer 22 surrounding inner conductor 21. Dielectric layer 22 may be constructed of Teflon or any other material suitable for use as a dielectric. Dielectric layer 22 is surrounded by an outer conductor 24 constructed of copper or any other suitable conductive material. Outer conductor 24 is surrounded by a shield 25 to electrically and thermally insulate outer conductor 24. Outer conductor 24, inner conductor 21, and dielectric 22 form a coaxial structure. Antenna 20 may further include a handle 26 (FIGS. 1 and 2) at the proximal end thereof to control the movement of antenna 20.

As shown in FIG. 3A, inner conductor 21 extends beyond the distal ends of dielectric layer 22, outer conductor 24, and shield 25, such that inner conductor 21 extends into balloon 50 when balloon 50 is attached to the distal end of antenna 20. Balloon 50 may include a flexible member 52 attached to the distal end of balloon 50. Alternatively, the distal end of flexible member 52 may be free floating. A further alternative may include inner conductor 21 attached to the distal end of balloon 50. Proximal end of flexible member 52 is configured to attach to distal end of inner conductor 21 through a banding process.

Figure 1:
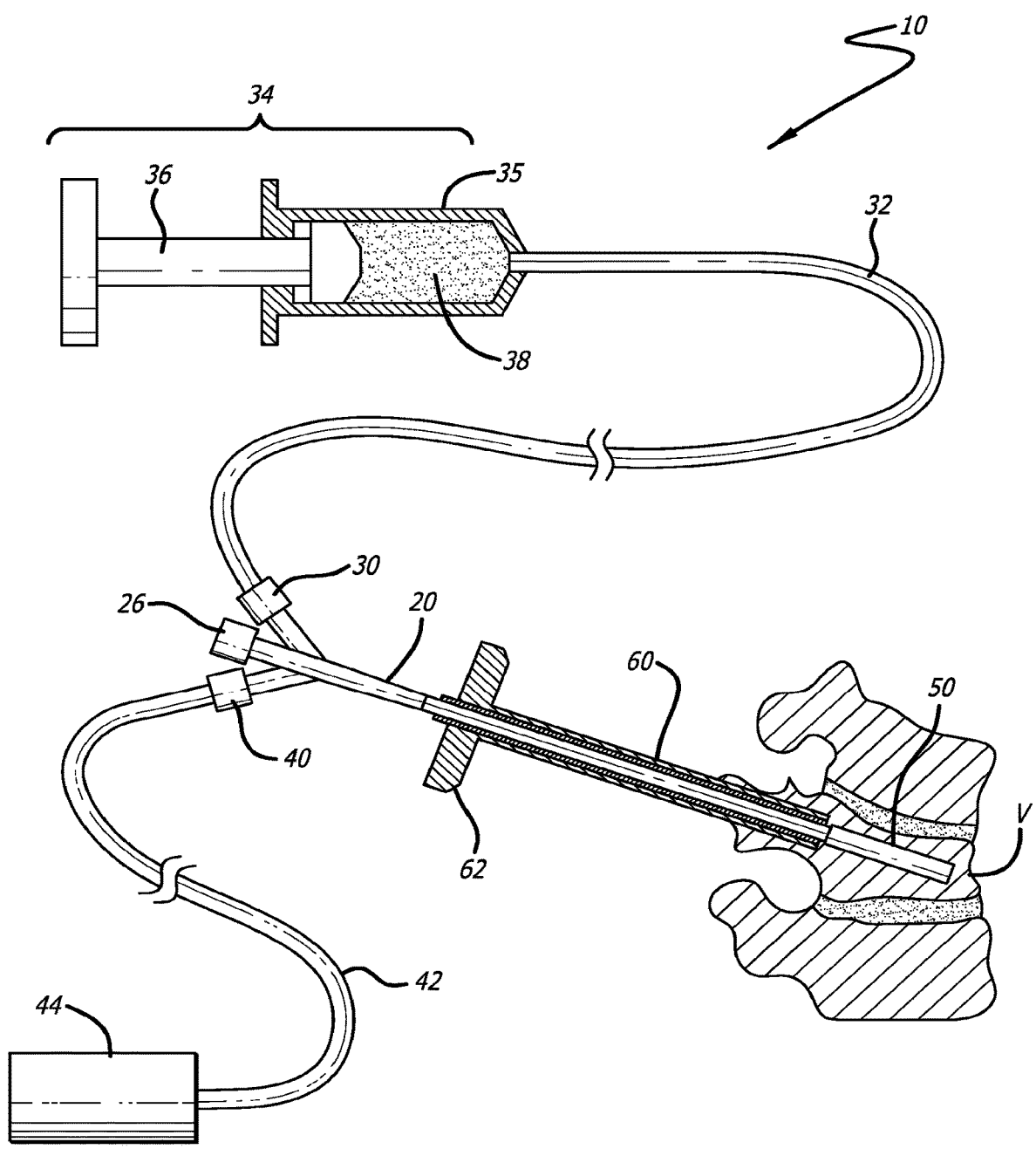
FIG. 1 is a partially cross-sectional elevational view of a system for use in tumor ablation and vertebral compression fracture repair in accordance with an embodiment of the present invention showing a microwave antenna with a balloon attached to the distal end thereof inserted into a fractured vertebral body and a high pressure syringe and microwave generator connected to the proximal end of the microwave antenna.

As shown in FIGS. 1 and 2, antenna 20 includes a fluid port 30 proximate the proximal end of antenna 20. Fluid port 30 facilitates attachment of a high pressure syringe 34 via tubing 32. High pressure syringe 34 includes a barrel 35 and a plunger 36. Fluid port 30 is in communication with a channel 23 (FIGS. 3A and 3B), or alternatively, multiple channels 23 (FIG. C). Channel 23 runs the length of antenna 20 through dielectric layer 22 and communicates with the interior of balloon 50. As such, pressing plunger 36 forces saline 38 and contrast material out of barrel 35 through tubing 32, fluid port 30, and channel 23, and into balloon 50. The increase of volume of saline 38 and contrast material in balloon 50 causes balloon 50 to inflate. The inflation of balloon 50 causes balloon 50 to apply pressure to the tumor, ensuring a good contact between balloon 50 and vertebral body V. Continued inflation of balloon 50 causes the cancellous bone to be pressed outward toward the cortical layer of fractured vertebral body V. Balloon 50 is inflated until fractured vertebral body V achieves the desired corrected height.

As shown in FIGS. 1 and 2, antenna 20 includes an energy port 40 proximate the proximal end of antenna 20. Energy port 40 facilitates attachment of a microwave generator 44 via a coaxial cable 42. Energy port 40 facilitates the transmission of microwave energy from coaxial cable 42 to inner and outer conductors 21 and 24. The microwave energy exits the distal end of antenna 20. The microwave energy exiting the distal end of antenna 20 heats the saline 38 within balloon 50. The heated saline 38 conducts heat to the tumor. The conducted heat is used to destroy the tumor. The microwave energy preferentially heats the saline and contrast mixture and therefore reduces the negative impact of microwave energy to adjacent vital structures. The direct heating effect of microwave ablation is replaced by indirect heating through conduction. As such, since most of the microwave energy is used to heat the saline and contrast mixture, the present invention will reduce harmful effects of microwave energy on the adjacent structures. In addition, performing the balloon inflation simultaneously with the ablation will reduce the duration of the procedure and may help the balloon kyphoplasty procedure as the bone softens. The temperature of the heated saline 38 may be monitored via a temperature probe (not shown) located at the distal end of the microwave antenna or at the distal end of outer conductor 24. The temperature inside balloon 50 may be monitored with a temperature sensing element such as RTD, TC, fiber optic thermometer or radiometry.

In a preferred embodiment of the present invention, system 10 is utilized in the following manner. The preferred method includes placing the patient in the prone position and making a small incision in the skin over fractured vertebral body V. The surgeon then inserts a cannula 60 through the incision into contact with fractured vertebral body V. The surgeon may manipulate the position of the cannula 60 by grasping a handle 62 located at the proximal end of cannula 60. When the cannula 60 is properly aligned, the surgeon introduces a drill (not shown) through cannula 60 and creates an opening in fractured vertebral body V and into the tumor. The surgeon withdrawals the drill and inserts antenna 20 through cannula 60 until balloon 50 is positioned within the opening created in fractured vertebral body V. With balloon 50 in the opening, the surgeon depresses plunger 36 on high pressure syringe 34, forcing saline 38 and the contrast material into balloon 50. The saline 38 inflates balloon 50, causing balloon 50 to press against the tumor. With balloon 50 pressing against the tumor, the surgeon turns on microwave generator 44. The microwave energy heats saline 38 in balloon 50. Saline 38 conducts the heat into the tumor. After the heat destroys the tumor, microwave generator 44 is turned off. At this point, the surgeon further depresses plunger 36, causing further inflation of balloon 50 until the correct height of fractured vertebral body V is achieved. When the correct height is achieved, balloon 50 is deflated and removed from fractured vertebral body V, leaving a larger cavity in fractured vertebral body V. The cavity in fractured vertebral body V is then filled with polymethyl methacrylate ("PMMA") bone cement.

Alternatively, the surgeon may continue reduction of fractured vertebral body V during the application of microwave energy. In addition, part or all of the procedure may be performed on both sides of fractured vertebral body V at the same time.

There is disclosed in the above description and the drawings, tumor ablation systems, which fully and effectively accomplish the objectives of this invention. It will be apparent, however, that variations and modifications of the disclosed embodiments may be made without departing from the principles of the invention or the scope of the appended claims.

What is claimed is:
1. A method of tumor ablation, the method comprising:
making an incision in skin of a patient;
creating an opening in a bone having a tumor;

inserting a portion of a microwave antenna system into the opening in the bone, the antenna system including a microwave antenna having a proximal end, a distal end opposite the proximal end, a length between the proximal end and the distal end, a first conductor terminating at an end at the distal end of the antenna, a second conductor terminating at an end positioned between the proximal end and the distal end of the antenna, a first channel and a second channel extending along at least a portion of the length of the antenna along and between portions of the first conductor and the second conductor, an energy port proximate the proximal end to connect the antenna to an energy source, a fluid port proximate the proximal end to connect the first channel and the second channel to a fluid delivery mechanism, an inflatable balloon attached to the antenna adjacent the end of the second conductor and having an interior fluidly communicating with the first channel and the second channel, and a flexible member extending distally from the first conductor and connecting to a distal end portion of the balloon in the interior thereof, the first conductor and the second conductor being coaxial with one another relative to a common axis, the first conductor extending along the axis, the second conductor being spaced apart from the axis, and the first channel and the second channel being closer to the axis than the second conductor;

positioning at least the balloon adjacent the tumor;

introducing a fluid through the fluid port and through the first channel and the second channel to inflate the balloon causing the balloon to apply pressure to the tumor;

applying energy through the energy port to one of the first conductor and the second conductor to heat the fluid in the balloon and heat the tumor;

constraining movement of the distal end portion of the balloon relative to the first conductor using the flexible member; and removing the microwave antenna system from the patient.

2. The method of claim 1, further comprising creating a cavity in the bone via the inflation of the balloon, and, after removal of the microwave antenna system from the patient, filling the opening and the cavity with bone cement.

3. The method of claim 1, wherein the energy is microwave excitation.

4. The method of claim 1, wherein the fluid is saline.

5. The method of claim 1, further comprising monitoring a temperature of the tumor.

6. The method of claim 5, further comprising heating the tumor to at least 50 degrees Celsius.

7. The method of claim 1, wherein the bone is a vertebral body.

8. The method of claim 1, wherein the creating the opening and inserting the portion of the microwave antenna system are performed through a cannula.

9. The method of claim 1, further comprising:
making a second incision in the skin of the patient;
creating a second opening in the bone;
inserting a portion of a second microwave antenna system identical to the microwave antenna system into the second opening in the bone;
creating a second cavity in the bone using the second microwave antenna system;
removing the second microwave antenna system from the patient; and after removal of the second microwave antenna system from the patient, filling the second opening and the second cavity in the bone with bone cement.

10. The method of claim 9, further comprising:
applying energy to the second antenna to heat the second fluid.

11. The method of claim 9, wherein the creating the second opening and inserting the portion of the second microwave antenna system are performed through a second cannula.

12. The method of claim 1, wherein the first conductor is positioned at least partially within the second conductor.

13. The method of claim 12, wherein the first channel and the second channel are positioned on opposite sides of the first conductor.

14. The method of claim 1, wherein the balloon includes a proximal end and a distal end, the proximal end of the balloon being attached to the antenna adjacent the end of the second conductor, and the distal end portion of the balloon being at the distal end of the balloon.

15. The method of claim 14, wherein the balloon has a maximum length between the proximal end and the distal end, and the flexible member extends over half the maximum length of the balloon.

16. A method of tumor ablation, the method comprising:
making an incision in skin of a patient;
creating an opening in a bone having a tumor;
inserting a portion of a microwave antenna system into the opening in the bone, the antenna system including a microwave antenna having a proximal end, a distal end opposite the proximal end, a length between the proximal end and the distal end, a first conductor terminating at an end at the distal end of the antenna, a second conductor terminating at an end positioned between the proximal end and the distal end of the antenna, at least one channel extending along at least a portion of the length of the antenna along and between portions of the first conductor and the second conductor, an energy port proximate the proximal end to connect the antenna to an energy source, a fluid port proximate the proximal end to connect the at least one channel to a fluid delivery mechanism, an inflatable balloon attached to the antenna adjacent the end of the second conductor and having an interior fluidly communicating with the at least one channel, and a flexible member extending distally from the first conductor and connecting to a distal end portion of the balloon in the interior thereof, the first conductor and the second conductor being coaxial with one another relative to a common axis, the first conductor extending along the axis, the second conductor being spaced apart from the axis, and the at least one channel being closer to the axis than the second conductor;

positioning at least the balloon adjacent the tumor;

introducing a fluid through the fluid port and through the at least one channel to inflate the balloon causing the balloon to apply pressure to the tumor and create a cavity in the bone;

applying energy through the energy port to one of the first conductor and the second conductor to heat the fluid in the balloon and heat the tumor;

constraining movement of the distal end portion of the balloon relative to the first conductor using the flexible member; and removing the microwave antenna system from the patient.

17. The method of claim 16, wherein the balloon includes a proximal end and a distal end, the proximal end of the balloon being attached to the antenna adjacent the end of the second conductor, and the distal end portion of the balloon being at the distal end of the balloon.

18. The method of claim 17, wherein the balloon has a maximum length between the proximal end and the distal end, and the flexible member extends over half the maximum length of the balloon.

19. A method of tumor ablation, the method comprising:
making an incision in skin of a patient;
creating an opening in a bone having a tumor;
inserting a portion of a microwave antenna system into the opening in the bone, the antenna system including a microwave antenna having a proximal end, a distal end opposite the proximal end, a length between the proximal end and the distal end, a first conductor terminating at an end at the distal end of the antenna, a second conductor terminating at an end positioned between the proximal end and the distal end of the antenna, at least one channel extending along at least a portion of the length of the antenna along and between portions of the first conductor and the second conductor, an energy port proximate the proximal end to connect the antenna to an energy source, a fluid port proximate the proximal end to connect the at least one channel to a fluid delivery mechanism, an inflatable balloon attached to the antenna adjacent the end of the second conductor and having an interior fluidly communicating with the at least one channel, and a flexible member extending distally from the first conductor and connecting to a distal end portion of the balloon in the interior thereof, the first conductor and the second conductor being coaxial with one another relative to a common axis, the first conductor extending along the axis, the second conductor being spaced apart from the axis, and the at least one channel being closer to the axis than the second conductor;
positioning at least the balloon adjacent the tumor;
inflating the balloon to cause the balloon to apply pressure to the tumor and create a cavity in the bone;
applying energy through the energy port to one of the first conductor and the second conductor to heat the tumor;
constraining movement of the distal end portion of the balloon relative to the first conductor using the flexible member; and
removing the microwave antenna system from the patient.

20. The method of claim 19, wherein the balloon includes a proximal end and a distal end, the proximal end of the balloon being attached to the antenna adjacent the end of the second conductor, and the distal end portion of the balloon being at the distal end of the balloon.

* * * * *